United States Patent [19]  
Okada

[11] 3,978,208  
[45] Aug. 31, 1976

[54] DEODORIZING COMPOSITIONS  
[75] Inventor: Masao Okada, Honjo, Japan  
[73] Assignee: Eisai Co., Ltd., Tokyo, Japan  
[22] Filed: Jan. 7, 1974  
[21] Appl. No.: 431,482

[52] U.S. Cl. .................... 424/76; 424/266; 424/298; 424/320; 424/327  
[51] Int. Cl.² .......................... A61L 13/00  
[58] Field of Search ............ 424/76, 298, 320, 327, 424/266

[56] References Cited  
UNITED STATES PATENTS

| | | | |
|---|---|---|---|
| 2,761,867 | 9/1956 | Mecca | 424/76 X |
| 2,998,390 | 8/1961 | Hamilton | 424/76 X |
| 3,172,817 | 3/1965 | Leupold et al. | 424/76 X |
| 3,431,208 | 3/1969 | Bailey | 424/76 X |
| 3,714,361 | 1/1973 | Morimoto et al. | 424/327 X |

FOREIGN PATENTS OR APPLICATIONS

| | | |
|---|---|---|
| 729,204 | 12/1942 | Germany |
| 1,037,899 | 8/1966 | United Kingdom |
| 23,863 | 1/1914 | United Kingdom |

OTHER PUBLICATIONS  
Kobashi et al., Chem. Abst. vol. 74 (1971).  
Detergents and Emulsifiers, McCutcheon (1963), pp. 44 and 126.  
The Chemistry and Manufacture of Cosmetics, Navarre, p. 179 (1942).

Primary Examiner—V. D. Turner  
Assistant Examiner—Allen J. Robinson  
Attorney, Agent, or Firm—Wenderoth, Lind & Ponack

[57] ABSTRACT

Novel deodorizing compositions to be used in excrementary pit or sink of lavatory of living houses, latrine, domestic animal and poultry houses, zoological garden, drainage and the like, as well as the commodation tank provided with aeroplane, ship, long distance omnibus, train, etc. The novel deodorizing compositions contain as active ingredient the derivatives of hydroxamic acid and additives including diluent, weighing and/or any other auxiliary materials.

8 Claims, No Drawings

DEODORIZING COMPOSITIONS

This invention relates to novel deodorizing compositions and more particularly to the deodorizing compositions effective for preventing offensive smell of excrement which may evolve everywhere such as pit or sink of the lavatory of living house, latrine, domestic animal and poultry houses, zoological garden, drainage, as well as the commodation tank provided in aeroplane, train, ship, long distance omnibus, ets. The deodorizing compositions of the instant invention contain as active ingredient the derivatives of hydroxamic acid and the additives including diluent, weighing and/or any other auxiliary materials.

Several methods and compositions have hitherto been proposed for preventing offensive smell in lavatory, latrine or the like, which usually contain as effective ingredient a volatile organic compound such as camphor, dichlorobenzene, naphthalene, perfume of essential oils and the like, which evolves aromatic or fragrant odor effective for masking bad smell of the excrement; adsorbing agents such as active carbon capable of adsorbing the bad smell; and acid chemicals such as acid salt, hydrochloric and oxalic acids which are capable of neutralizing gases of the bad smell.

It was, however, found that these known methods and compositions have drawbacks in that the masking effect to the bad smell attained by the fragrant odor of the organic volatile substances is merely a superficial camouflage and not a true elimination of the bad-smelling gaseous substances evolved as the decomposition products of excrement; whereas use of the acid chemicals such as hydrochloric acid is not only hazardous in dealing with but also has a tendency of chemical corrosion on the concrete and metallic materials used for construction of the equipments. After all, it should be said that these known methods for deodorizing the bad smell are not satisfactory.

Having regard to the actual status of the known arts for the deodorization of the bad smell as aforementioned, the inventor of this invention had attended upon improvement of the known methods. The inventor then had surprisingly found that the derivatives of hydroxamic acid are highly effective for preventing formation of gaseous products of offensive odor as decomposition product of the excrement held in the sink of lavatory, latrine, the commodation tank or the like.

Accordingly, the primary object of this invention is to provide a novel deodorizing composition free from hazard in handling and having durable and high activity of preventing evolution of offensive smells.

The so-called "derivatives of hydroxamic acid" used throughout the specification and claims of this invention are meant by the substances represented by the formula

R—CONHOH wherein R stands for alkyl, aryl and pyridyl, although other functional radicals may equally be permissible.

Following chemical compounds may be enumerated as typical of the derivatives of hydroxamic acid to be intended but without limitation:
p-Nitrobenzohydroxamic acid,
p-Chlorobenzohydroxamic acid,
p-Methoxybenzohydroxamic acid,
Nicotinohydroxamic acid,
Acetohydroxamic acid,
Caprylohydroxamic acid,
o-Methylbenzohydroxamic acid,
o-Chlorobenzohydroxamic acid,
o-Aminobenzohydroxamic acid, and
Benzohydroxamic acid.

In contradistinction to the known deodorizing methods which unexceptionally depend upon the afterward treatment of the gaseous products of offensive smell once produced by the decomposition of excrement, the deodorization effected by the novel compositions of the present invention is based on the fact that the derivatives of hydroxamic acid act or function as inhibitor of formation of ammonia from the excrement due to decomposition. It is believed that such function as the inhibitor of formation of ammonia represented by the composition of the present invention relies upon antiurease activity of the derivatives of hydroxamic acid contained therein.

In practice of this invention, the intended deodorizing compositions may be provided in various forms such as the liquid, suspension, powdery and solid preparations. The contents of the derivatives of hydroxamic acid as the active agent in the preparations may vary within the range of 2 – 20 % depending upon degrees of offensive smell where the compositions are intended to be utilized such as the pits of lavatory, latrine, livestock houses as well as the commodation tank of aeroplane, etc. Powdery preparation may thus contain, for example, 5 – 20 % of derivative(s) of hydroxamic acid, 1 – 10 % of perfume and the remainder of a powdery diluent or weighing material such as pulverized talc, anhydrous silica, kaolin, calcium carbonate or the like, all % being percent by weight; a liquid preparation may contain, for example, 5 – 20 % of hydroxamic derivative, 1 – 10 % of perfume with or without an amount of surfactant and the remainder of water.

Although any surfactant may be used for the purpose aforementioned, so far as the same is capable of dispersing homogeneously the hydroxamic acid derivative and perfume to be employed, there may usually be employed sorbitan esters of fatty acid (Span type surfactant), ethylene oxide adduct of sorbitan ester of fatty acid (Tween type surfactant), ethylene oxide adduct of castor oil HCO type surfactant; diethanol amide of laurylsulfuric acid and sodium salt of lauryl sulfuric acid.

Beneficial deodorizing effect achievable by the composition will be explained in more concrete manner, wherein Perfume-VF used as typical was a commercial product having essentially the following constituents:

| | |
|---|---|
| alcohols essentially of geraniol | 27(%) |
| Esters essentially of linalyl acetate | 19 |
| Phenols essentially of eugenol | 3 |
| Aldehydes essentially of cyclamine aldehyde | 4 |
| Ketones essentially of ionone | 3 |
| Ethers essentially of diphenyl oxide | 3 |
| Hydrocarbon essentially of caryophyllene | 4 |
| Natural essences essentially of cedar wood oil | 27 |
| Others essentially of musk xylol | 10 |
| Total | 100% |

EXPERIMENT 1 a. 100 Bottles were prepared each containing 100 g. of the following composition, Composition A:

| | |
|---|---|
| Acetohydroxamic acid | 4.0 g. |
| Perfume-VF | 1.6 g. |
| Water sufficient to make up total | 100.0 g. | b. 100 Bottles were prepared each containing 100 g. of the following composition, Control A:

| | |
|---|---|
| Perfume-VF | 1.6 g. |
| Water sufficient to make up total | 100.0 g. |

The contents of the total 200 bottles were respectively added to 200 lavatory pits of dip up system without ventilator of the same size equipped to the uniform living houses, the houses having been installed by the Public Building Society. After the additions of the compositions, the conditions of evolution of offensive smell were daily inspected for a week through vital function. The results obtained are shown in Table 1, wherein the figures given in the columns 2 and 3 show the houses where the offensive smells were inspected at the corresponding inspection days in the week given in column 1.

Table 1

| Days elapsed | Composition A | Composition of Control A |
|---|---|---|
| 1 | 0 | 92 |
| 2 | 5 | 8 |
| 3 | 11 | 0 |
| 4 | 22 | 0 |
| 5 | 36 | 0 |
| 6 | 19 | 0 |
| more than 6 | 7 | 0 |

As is evident from the above data, the considerable deodorizing effect with durability for a long time is attained by the use of the composition according to the present invention.

EXPERIMENT 2

About 11 kg. of the aqueous composition were prepared each 100 g. of which contained 5.0 g. of benzohydroxamic acid, 1.6 g. of Perfume-VF and the remainder of water.

100 g. of said aqueous composition were respectively added to 100 lavatory pits similar to those used in the preceding Experiment. The days lapsed from the addition of said aqueous composition were checked for individual pit when offensive odor became smell. At that every occasion, each 100 g. of said same aqueous composition were added once more to the detected individual pit. Then the days lapsed from said second addition of the composition were checked for individual pit when offensive odor became smeel. At that every occasion, each 100 g. of said same aqueous composition were still once more added to the detected individual pit. After then the days lapsed from said third addition of the composition were checked for individual pit when offensive odor again became smell.

The data of the inspection are listed in Table 2.

Table 2

| First addition | | Second addition | | Third addition | |
|---|---|---|---|---|---|
| Days from first addition | Number of pits with bad smell | Days from first addition | Number of pits with bad smell | Days from first addition | Number of pits with bad smell |
| 2–3 | 18 | | | | |
| 4–5 | 51 | 4–5 | 0 | 6–7 | 0 |
| 5–6 | 23 | 6–7 | 2 | 8–9 | 0 |
| 7–8 | 7 | 8–9 | 13 | 10–11 | 3 |
| 9 | 1 | 10–11 | 24 | 12–13 | 9 |
| | | 12–13 | 42 | 14–15 | 26 |
| | | 14–15 | 18 | 16–17 | 34 |
| | | 16–17 | 1 | 18–19 | 23 |
| | | | | 20–21 | 5 |

In view of the data depicted in Table 2, it is noted that only 3 %, at the worst, of the 100 treated pits expelled the bad-smell after 10 – 11 days from the first addition of the composition; 5 % at the best, of the treated 100 pits expelled the bad smell after 20 – 21 days from the first addition of the composition. Furthermore, most of the 100 treated pits, that is, 83 % of the treated total pits were effectively prevented from the evolution of the bad smell for 14 – 19 days from the first addition of the composition.

From the fact as aforementioned, it may be expected that offensive smell from the pits of lavatories equipped in the living houses, for example, can effectively be prevented by about 3 time additions within adequate intervals for a month of each 100 g. of an aqueous deodorizing composition which contains, for example, 4 – 5 % by weight of a derivative of hydroxamic acid according to the present invention.

The deodorizing compositions of the present invention may be used not only in the pit or sink of lavatory of usual living house, hotel, school, hospital and the like, but also the commodation tank provided in vehicles such as aeroplane, train, long distance omnibus and ship.

The prevention of bad smell of such commodation tank is of very serious problem especially in aeroplane and ship passing through the equator or the tropics where the atmospheric temperatures are considerably high. It was found that the conventional masking agent used as deodorizing agent is almost useless for a certain long time service required therefor.

Following experiment 3 on deodorization was conducted at elevated atmospheric temperature such as that encountered in the vehicles passing through the tropics. A deodorizing composition of the present invention was employed in this experiment in comparison with the hitherto known masking agents.

EXPERIMENT 3 a. Formulation of the composition, Composition A, of the present invention provided for commodation tank in aeroplane:

| | |
|---|---|
| Acetohydroxamic acid | 7.5 g. |

-continued

| | |
|---|---|
| Sodium lauryl sarcosine | 6.5 g. |
| Indigocarmine | 2.0 g. |
| p-Chloro-m-xylenol | 0.2 g. |
| Perfume-VF | 2.0 g. |
| Starch | 31.5 g. |
| Total | 50.0 g. | b. DF-Powder 50, Composition B, as comparison, which is a commercial product manufactured by Per-machem Asia Company.

c. Formulation for control, Composition C:

| | |
|---|---|
| Sodium lauryl sarcosine | 6.5 g. |
| Indigocarmine | 2.0 g. |
| p-Chloro-m-xylenol | 0.5 g. |
| Perfume-VF | 2.0 g. |
| Starch | 38.0 g. |
| Total | 50.0 g. | d. Water as control, Control D.

Procedure of the experiment was as follows:

Each 10 g. of fresh faeces taken after 2 – 5 minute elapse of excretion were placed respectively in 5 conical flasks of about 150 ml. capacity and kneaded respectively with the above Compositions A and B and Controls C and D.

Each of the contents of the flasks was diluted with an amount of fresh urine to make up total 100 ml. The openings of the flasks were sealed with a sheet of aluminum foil and then tightened up with an elastic string of rubber. The flasks were kept for a period at the temperature of 50° ± 1°C., an imaginary temperature in the water-closet of aeroplane especially landed on an area of the tropics.

During the keeping while, the amount of gaseous ammonia evolved and accumulated in the space of the flasks was respectively and successively determined by means of a gas-detecting and measuring tube having a capacity of 100 ml. aspiration of a gaseous carrier. The tube used was that made by Nishio Industrial Company.

The results of the observation are listed in Table 3.

Table 3

| Times (hours) for keeping | Quantity in ppm of NH$_3$ determined | | | |
|---|---|---|---|---|
| | Composition A | Composition B | Composition C | Control D |
| 0.5 | 90 | 250 | 250 | 240 |
| 1.0 | 80 | 560 | 580 | 580 |
| 1.5 | 100 | >600 | >600 | >600 |
| 2.0 | 100 | — | — | — |
| 2.5 | 130 | — | — | — |
| 2.75 | 230 | — | — | — |
| 3.0 | >600 | — | — | — |

As is seen from the data given in Table 3, the deodorizing composition, Composition A, of the present invention, when compared with the hitherto known deodorizing composition, is considerably effective to reduce the formation of ammonia in the excrement pit at an elevated temperature for an increased durability. The composition is thus particularly useful as deodorizing agent in the commodation tank of a long distance aeroplane. Difficulty in this respect where the hitherto known masking agent has been employed may advantageously be removed by substituting it with the novel composition of the present invention.

For a long time use such as for 20 – 30 hours, as in the case of aeroplane entering service in a long distance international air line, for example, use of the composition is preferable which contains a high concentration of the derivative of hydroxamic acid as active ingredient and/or an ordinary composition may be used successively and portionwisely. In this respect, it should be noted that the deodorizing compositions of the present invention, different from the hitherto known products which merely superficially masking the bad smell with their strong stimulant fragrance, suppress evolution of free ammonia that may produce by destructive decomposition of the excrement resulting in an essential source of unpleasant odor.

Additional advantage of the compositions of the present invention that cannot be overlooked is in their non-toxicity to men and beasts and ease to deal with.

The deodorizing compositions of this invention can broadly be used not only in the excrement pits of lavatory, latrine and the like and the commodation tank of the vehicles as aforementioned, but also in sewer and vegetable manure heap, in order to prevent formation of offensive smell.

The following examples are illustrative of the invention, which are not to be construed limitation of the invention, percents being by weight.

EXAMPLE 1

| | |
|---|---|
| Acetohydroxamic acid | 10 % |
| Talc | 88 % |
| Perfume-VF | 2 % |

The ingredients are thoroughly mixed together to form an evenly distributed powdery composition.

About 30 g. of the resulting composition may be spread to the lavatory pit of living house immediately after clearing by dipping up the excrement.

EXAMPLE 2

| | |
|---|---|
| Caprylohydroxamic acid | 5 % |
| Kaolin | 93 % |
| Perfume-VF | 2.0 % |

The ingredients are thoroughly mixed to a powdery deodorizing composition. The composition thus obtained may be used as that of the preceding Example.

EXAMPLE 3

| | |
|---|---|
| Acetohydroxamic acid | 5 % |
| Benzohydroxamic acid | 2.5 % |
| Talc | 90.5 % |
| Perfume-VF | 2 % |

The ingredients are thoroughly mixed to a powdery composition.

EXAMPLE 4

| | |
|---|---|
| Acetohydroxamic acid | 5.0 g. |
| Perfume-VF | 2.0 g. |
| Laurylsulfuric acid diethanol amide | 5.0 g. |
| Water sufficient to make up total | 100.0 ml. |

30 g. of the liquid composition thus obtained may be used, a time while well shaking, as in the case of the composition of Example 1.

EXAMPLE 5

| | |
|---|---|
| Acetohydroxamic acid | 5.0 g. |
| Caprylohydroxamic acid | 2.5 g. |
| Perfume-VF | 2.0 g. |
| Sodium lauryl sulfate | 6.0 g. |
| Remainder of water to make up total | 100.0 ml. |

The ingredients are thoroughly mixed to obtain a liquid composition.

EXAMPLE 6

| | |
|---|---|
| p-Chlorohydroxamic acid | 4.0 g. |
| Acetohydroxamic acid | 4.0 g. |
| Perfume-VF | 2.0 g. |
| Tween 80 | 5.0 g. |
| Water sufficient to make up total | 100.0 ml. |

EXAMPLE 7

| | |
|---|---|
| Acetohydroxamic acid | 5.0 g. |
| Caprylohydroxamic acid | 3.5 g. |
| Sodium lauroyl sarcosine | 7.0 g. |
| Indigocarmine | 2.0 g. |
| p-Chloro-m-xylenol | 0.5 g. |
| Perfume-VF | 2.0 g. |
| Starch | 30.0 g. |

The ingredients are well mixed to obtain a powdery composition used for commodation tank of aeroplane.

Perfume-VF employed as one of the ingredients of the compositions given in the above Examples may be substituted by an equivalent amount of any other known perfumes prepared, for example, by suitably blending natural and synthetic essential oils such as citronellol, benzyl actate, cinnamic aldehyde and coumarin other than those contained in Perfume-VF as aforementioned.

What is claimed is:

1. A powdery deodorizing composition consisting of

| | |
|---|---|
| acetohydroxamic acid | 10 % by weight |
| Pulverized talc | 88 % by weight |
| perfume | 2 % by weight. |

2. A method of deodorizing the excrement pits of lavatories, latrines, live-stock houses, zoological gardens, drainages or commodation tanks of vehicles which comprises applying thereto an effective deodorizing amount of the composition of claim 1.

3. An aqueous deodorizing composition consisting of

| | |
|---|---|
| acetohydroxamic acid | 5.0 g. |
| laurylsulfuric acid diethanol amide | 5.0 g. |
| perfume | 2.0 g. |
| water sufficient to make up total | 100.0 ml. |

4. A method of deodorizing the excrement pits of lavatories, latrines, live-stock houses, zoological gardens, drainages or commodation tanks of vehicles which comprises applying thereto an effective deodorizing amount of the composition of claim 3.

5. An aqueous deodorizing composition consisting of

| | |
|---|---|
| acetohydroxamic acid | 5.0 g. |
| caprylohydroxamic acid | 2.5 g. |
| sodium lauryl sulfate | 6.0 g. |
| perfume | 2.0 g. |
| water sufficient to make up total | 100.0 ml. |

6. A method of deodorizing the excrement pits of lavatories, latrines, live-stock houses, zoological gardens, drainages or commodation tanks of vehicles which comprises applying thereto an effective deodorizing amount of the composition of claim 5.

7. A powdery deodorizing composition to be used for the commodation tank of vehicles, consisting of

| commodation tank of vehicles, consisting of | |
|---|---|
| acetohydroxamic acid | 5.0 parts by weight |
| caprylohydroxamic acid | 3.5 parts by weight |
| sodium lauroyl sarcosine | 7.0 parts by weight |
| Indigocarmine | 2.0 parts by weight |
| p-chloro-m-xylenol | 0.5 parts by weight |
| perfume | 2.0 parts by weight |
| starch | 30.0 parts by weight. |

8. A method of deodorizing the excrement pits of lavatories, latrines, live-stock houses, zoological gardens, drainages or commodation tanks of vehicles which comprises applying thereto an effective deodorizing amount of the composition of claim 4.

* * * * *